United States Patent [19]

McCain et al.

[11] 4,453,023

[45] Jun. 5, 1984

[54] PROCESS FOR PREPARING NONIONIC SURFACTANTS-OXYALKYLATION WITH PROMOTED BARIUM CATALYSTS

[75] Inventors: James H. McCain; Louis F. Theiling, Jr., both of Charleston, W. Va.

[73] Assignee: Union Carbide Corporation, Danbury, Conn.

[21] Appl. No.: 454,573

[22] Filed: Dec. 30, 1982

[51] Int. Cl.$^3$ .............................................. C07B 41/03
[52] U.S. Cl. .................................... 568/618; 568/619; 568/620; 568/622; 568/623; 568/624; 568/625
[58] Field of Search ............... 568/618, 619, 620, 622, 568/625

[56] References Cited

U.S. PATENT DOCUMENTS

| | | | |
|---|---|---|---|
| 2,934,505 | 4/1960 | Gurgiolo | 568/618 UX |
| 3,100,750 | 8/1963 | Bailey et al. | 568/628 |
| 3,328,306 | 6/1969 | Ellis | 568/618 |
| 4,210,764 | 7/1980 | Yang et al. | 568/618 |
| 4,223,164 | 9/1980 | Yang et al. | 568/618 |
| 4,302,613 | 11/1981 | Yang et al. | 568/618 |

FOREIGN PATENT DOCUMENTS

| | | | |
|---|---|---|---|
| 34649 | 2/1981 | European Pat. Off. | |
| 34648 | 2/1981 | European Pat. Off. | |
| 26546 | 4/1981 | European Pat. Off. | 568/618 |

*Primary Examiner*—Howard T. Mars
*Attorney, Agent, or Firm*—Jean B. Mauro

[57] ABSTRACT

The process for preparing nonionic surfactants wherein a narrower molecular weight distribution is obtained by the use of a barium catalyst which comprises reacting a reactive hydrogen compound selected from the group consisting of monohydric alcohols having from about 8 to about 20 carbon atoms and a difunctional polypropylene oxide polymer having an average molecular weight in the range of 1000 to 5000 with an alkylene oxide having 2 to 4 carbon atoms at a temperature at which the reaction proceeds in the presence of at least a catalytic amount of a barium salt selected from the group consisting of barium hydroxide, barium alkoxides, barium phenoxides, hydrates thereof or mixtures thereof and a catalytic amount of an oxyalkylation catalyst promoter.

7 Claims, No Drawings

PROCESS FOR PREPARING NONIONIC SURFACTANTS-OXYALKYLATION WITH PROMOTED BARIUM CATALYSTS

DESCRIPTION

1. Field of the Invention

The present invention relates to a process for the preparation of nonionic surfactants wherein the molecular weight distribution of the nonionic surfactants obtained is narrower than that obtained by use of only barium salt as the oxyalkylation catalyst.

2. Background of the Invention

The instant invention relates to the preparation of improved nonionic surface active agents and, more particularly, to a process for the oxyalkylation of certain reactive hydrogen compounds to prepare nonionic surface active agents having lower pour points, wherein the molecular weight distribution is narrower than that obtained with barium catalysts employed heretofore.

Low molecular weight condensation products of an alkylene oxide, particularly ethylene oxide, or mixtures of alkylene oxides, such as ethylene and propylene oxide, with an alcohol are well known and for a long time have been prepared commercially for use in detergents, cleansing agents, dry cleaning materials, wetting and emulsifying agents and the like. These products are conventionally produced by reacting the reactive hydrogen compound with the alkylene oxide in the presence of a strongly alkaline or an acidic catalyst. Such preparative procedures result in the production of a mixture of relatively low molecular weight (up to about 5000) condensation product species containing a number of alcohol derivatives having different molecular proportions of alkoxylate. Thus, the reaction products generally obtained are, in reality, a mixture of derivatives of the alcohol moiety containing different molecular proportions of alkylene oxide units, i.e., having varying molar ratios of alcohol to alkylene oxide, and a wide range of molecular weights as well as having a certain proportion of unreacted alcohol. Moreover, as is well known, the conventional designation of the number of alkylene oxide units present per molecule of an alcohol alkoxylate is a designation of the average number of alkylene oxide units per molecule. A substantial proportion of the alcohol alkoxylates present are generally present as alcohol alkoxylates having a greater and a lesser number of alkylene oxide units present than the actual average value would indicate. The designations of such products is well understood in the art and will be employed herein consistent with the well understood meaning.

It is generally desirable to restrict, i.e. control the breath of the molecular weight distribution, the mixture to adjacent analogues of the desired product insofar as possible, since, as is well known, the number of moles of alkylene oxide in the reaction product is a major factor in determining that the chemical and physical properties of such products are, but, as a matter of course, it is quite difficult to control the molecular weight distribution. Acidic catalysts tend to give a narrower molecular distribution than alkaline catalysts, but, unfortunately, also contribute to the formation of undesired by-products. Thus, alkaline catalysts, which are typically a strong base such as alkali metal hydroxides and alcoholates, are generally used as the more efficient type of oxyalkylation catalyst. Unforunately, the molecular distribution of the products are more diffuse, containing a greater proportion of lower and higher molecular weight species and smaller amounts of the species with the desired number of moles of alkylene oxide per mole of alcohol. For example, an eight-mole ethylene oxide (EO) adduct per mole of 1-dodecanol will contain not only the 8-mole EO adduct specie but also lower mole adducts and higher mole adducts. Lower mole adducts in the product mixture will range down to the one-mole adduct and higher adducts will extend up to 14 or 15 and beyond. The molecular weight distribution is a measure of the relative amounts of the various adducts in the product mixture and can be represented in the form of a generally bell-shaped curve where the amount of each adduct species is plotted versus the number of moles of epoxide in a species or of a description of the relative amount of each individual adduct. When the molecular weight distribution is characterized by a bell-shaped curve, a narrower distribution gives a sharper curve, which is higher at the middle and lower at the ends. A broader distribution curve would be lower at the middle portion of the range and higher at the ends, and such is not desirable.

Heretofore, several methods have been suggested for providing reaction products of an active hydrogen compound, e.g., alcohol, and epoxides which have a narrower range of molecular weights and molecular distribution of the epoxide units, and/or which reduce or eliminate the production of undesirable poly(alkylene glycol) and cyclic and straight chain ether by-products. For example, in U.S. Pat. No. 4,112,231 to Weibull et. al. it is disclosed that the use of certain neutral inorganic fluoborate and perchlorate salts will catalyze the reaction of epoxides with active hydrogen compounds to give products having a relatively narrower molecular distribution; i.e., a more limited range of molecular species and a larger proportion of desired molecular species; in U.S. Pat. No. 3,682,849 to Smith et al improved ethoxylated derivatives of $C_{11}$–$C_{18}$ alcohols are prepared by removing unreacted alcohol and lower ethoxylates from the ethoxylate mixture prepared by conventional methods by use of vapor phase separation techniques; in U.S. Pat. No. 2,870,220 to Carter, a two-stage process is disclosed for preparing monoalkyl ethers of ethylene glycol and polyethylene glycols of more restricted molecular weight range wherein an alkanol and ethylene oxide is reacted in the presence of an acidic catalyst during the first stage and then in the second-stage after removal of acid catalyst and unreacted alkanol, reacting the mixture with ethylene oxide in the presence of an alkali metal alcoholate of the initial alkanol; and in United Kingdom Pat. No. 1,501,327 to Laemmle et. al. there is disclosed a method of preparing mono- and poly-glycol ethers substantially free of undesired alkylene glycol by-products which method involves heating a reaction mixture containing an alkylene oxide and an alcohol in the presence of a catalyst containing alkali or alkaline earth cations wherein some or all of the catalyst is an anhydrous high boiling liquid residue prepared by concentrating the liquid residue from the same or different etherification processes after removal of the glycol ether product from the reaction mixture. None of the above-described processes and special catalysts disclosed in the art, however, are completely satisfactory in preparing a product with a desired molecular distribution in that such generally require multi-stage procedures or special acid-resistant equipment, may form undesirable by-products or simply do not provide sufficient control over the molecular weight distribution to be of a satisfactory nature. Thus, it would be highly desirable to develop a process wherein the reaction of an alkylene oxide (epoxide) with an alcohol could be more readily carried out to prepare surfactant products that have a relatively narrower molecular weight distribution of analogue species and contain only small amounts, at most, of undesirable poly(alkylene glycol) and ether by-products.

Recently, several patents were issued which are concerned with the preparation and advantages of nonionic surfactant products having a narrower molecular weight distribution. For example, U.S. Pat. No. 4,239,917 to Yang discloses the use of a class of basic barium materials as catalysts in the preparation of reaction products of alcohols and ethylene oxide so as to provide a product with a narrow, high mole adduct distribution while providing relatively low levels of undesirable by-products and unreacted free alcohol. The molcular weight distribution factor of the products produced during the oxyalkylation reaction is discussed at length by patentee and the differences in the molecular weight distribution of reaction products prepared with conventional alkali metal catalysts, such as sodium hydroxide, and those prepared using a barium catalyst of the invention is shown by graphical representations. The patent, to Yang, also shows that other alkaline earth metal materials, such as calcium hydroxide, magnesium oxide, and strontium hydroxide, were ineffective as catalysts for the oxyalkylation reaction. Thus, patentee demonstrates that significant differences exist in the catalytic effectiveness between even the various alkaline earth metals and not only between the barium catalysts of the invention and alkali metal hydroxides.

Further, U.S. Pat. Nos. 4,210,764 and 4,223,164 to Yang et al are concerned with the problem of the molecular weight distribution of products prepared by oxyalkylation of alcohols using conventional alkaline catalysts and are directed to overcoming an induction period problem frequently observed when employing barium-containing catalysts, such as those disclosed in U.S. Pat. No. 4,239,917. The patentees suggest the use of various phenols for use as a promoter for the barium-containing catalyst to overcome the induction period difficulty. U.S. Pat. No. 4,223,164 discloses that with such promoters that certain basic strontium materials may also be employed as a catalyst for the oxyalkylation reaction.

Thus the above-discussed patents have disclosed pronounced differences in catalytic activity between the various alkaline earth metals and alkaline materials, in general, during the reaction of alkylene oxides with alcohols as well as the significant differences in the products prepared using a conventional alkali metal catalysts relative to those products prepared in the presence of alkaline earth metal materials which exhibit catalytic activity. The detailed discussion by patentees concerning control of the molecular weight distribution of the products prepared during the oxyalkylation reaction serves to detail the differences that exist between those products which are obtained by careful catalyst selection and the differences in product properties that may be realized by simply employing varying proportions of alkylene oxide in the reaction.

A process for preparing nonionic surfactants having a relatively narrower molecular weight distribution is disclosed in copending U.S. Ser. No. 079,539, filed Sept. 27, 1979, wherein nonionic surfactants are prepared by use of a basic salt of an alkaline earth metal selected from the group consisting of calcium, strontium, and barium alkoxides, calcium, strontium, and barium phenoxides and mixtures of the same. A process is disclosed in copending U.S. Ser. No. 275,031, filed June 18, 1981, wherein a soluble basic salt of barium is prepared for use as an oxyalkylation catalyst.

The above processes are to be distinguished from the instant invention wherein oxyalkylation catalyst promoters are employed with a barium catalyst to obtain a product with a relatively narrower molecular weight distribution.

SUMMARY OF THE INVENTION

This invention provides a process and the catalyst for carrying out the process for the preparation of nonionic surfactants having a molecular weight distribution which is narrower than that normally obtained by only the use of a barium catalyst. The process comprises reacting a reactive hydrogen compound selected from the group consisting of monohydric alcohols having between about 8 and about 25 carbon atoms, both branched and linear, and a difunctional polypropylene oxide polymer having an average molecular weight in the range of 1000 to 5000 with an alkylene oxide having 2 to 4 carbon atoms at a temperature at which the reaction proceeds in the presence of at least a catalytic amount of a barium catalyst selected from the group consisting of barium alkoxides, barium phenoxides, barium hydroxide, hydrates thereof or mixtures thereof, and an oxyalkylation promoter (an acid phosphorus compound), as discussed hereinafter. Preferably the barium catalyst and the oxyalkylation promoter are soluble in the reactants and the reaction products.

It has been discovered that the use of the above-noted barium catalysts as the barium component of the oxyalkylation catalyst as hereinafter described, in conjunction with certain acid phosphorus compounds (as oxyalkylation promoters), as hereinafter described, provide a promoted oxyalkylation catalyst that not only catalyzes the reaction of the active hydrogen compound with the alkylene oxide but also results in the formation of products having a narrower molecular weight distribution, i.e., a more limited range of molecular species and a larger proportion of the desired species in the reaction product, than that which is prepared with conventional alkali metal catalysts, such as potassium hydroxide, and than that which is prepared by use of only the barium salt as the oxyalkylation catalyst. In addition, in many instances the rate to products; i.e., surface active agents, is increased relative to those observed for conventional alkali metal catalysts and the basic salts of barium. Moreover, the process of the instant invention can be readily carried out in a single stage with substantially no delay or induction period, and without the need for special acid-resistant preparatory equipment. The products produced thereby have been found, in general, to exhibit improved properties, such as lower pour points, and to contain relatively small amounts of undesired poly(alkylene glycol) and ether by-products, such as those which are normally formed when acid compounds are used as the oxyalkylation catalyst.

DETAILED DESCRIPTION OF THE INVENTION

This process comprises reacting a reactive hydrogen compound selected from the group consisting of monohydric alcohols having between about 8 and about 25 carbon atoms, more preferably between about 8 and about 20 carbon atoms and/or a difunctional poly(propylene oxide) polymer having an average molecular weight in the range of 1000 to 5000 with an alkylene oxide having 2 to 4 carbon atoms in the presence of an oxyalkylation catalyst comprising a catalytically effective amount of a barium alkoxide, barium phenoxide, barium hydroxide, hydrates thereof or mixtures thereof and a catalytically effective amount of an oxyalkylation promoter selected from the group consisting of super phosphoric acid, phosphoric acid, diphosphoric acid, triphosphoric acid, phosphorous acid, dihydrogen phosphate compounds and oxides of phosphorous (e.g. $P_2O_5$, $P_2O_3$), and salts thereof, as hereinafter more fully discussed, carbon dioxide and oxalic acid. The oxalkylation promoter is believed to provide a poly-functional anion in situ, although the exact nature of the in situ species and reaction is not clearly understood.

The reaction may be conducted in a conventional manner, that is, the reactive hydrogen compound and the oxyalkylation catalyst (the term "oxyalkylation catalyst" is meant to include both the use of a catalyst of the instant invention wherein an oxyalkylation promoter, as hereinbefore defined, is employed and those compounds previously employed in the art as oxyalkylation catalysts) are placed in a reactor, the selected alkylene oxide is added to the reaction mixture until the desired number of moles have been reacted with the reactive hydrogen compound, and the product is removed from the reactor and neutralized. The reaction may be conducted in the presence of a solvent, but usually a solvent is not necessarily employed. The process may be carried out in a batch manner or in a continuous mode of operation.

The temperature at which the reaction proceeds is not narrowly critical and generally products can be made at a reasonable rate of reaction and without decomposition of the reactants or reaction products at a temperature between about 50° C. and about 400° C., with a temperature between about 100° C. and about 200° C. being generally preferred. While the pressure of the reaction is not narrowly critical when low-boiling epoxides, such as ethylene oxide and propylene oxide are employed, a pressurized reactor is preferably used. The ethylene oxide pressure, in general, depends on the selected temperature and the amount of unreacted ethylene oxide with a pressure between about 10 psig and about 100 psig being generally preferred.

The reaction product may be neutralized with any acid that will convert the oxyalkylation catalyst to a neutral salt, as for example, acetic acid, or quantities of carbon dioxide, sulfuric acid, and/or phosphoric acid.

Alcohols which are suitable for use in the practice of the invention as the reactive hydrogen compound are primary and secondary aliphatic alcohols which are straight or branched chain and have between about four and about twenty five carbon atoms. Exemplary of such alcohols are those derived by hydrogenation of natural fats and oils, such as CO and TA alcohols, trademark of and soldy by Proctor and Gamble Co., such as CO-1214N alcohol, CO-1618 alcohol, and TA 1618 alcohol, and ADOL alcohols, trademark of and sold by Ashland Oil Co., such as ADOL 54 alcohol, ADOL 61 alcohol, ADOL 64 alcohol, ADOL 60 alcohol and ADOL 66 alcohol. Alcohols produced by Ziegler chemistry can also be alkoxylated. Examples of these alcohols are ALFOL alcohols, trademarks of and sold by Contiental Oil Co., such as ALFOL 1012 alcohol, ALFOL 1214 alcohol, ALFOL 1412 alcohol, ALFOL 1618 alcohol, ALFOL 1620 alcohol; and EPAL alcohols, trademark of and sold by Ethyl Chemical Co., such as EPAL 1012 alcohol, EPAL 1214 alcohol, EPAL 1418 alcohol. The invention is extremely useful for oxo alcohols (hydroformylation) produced from olefins. Examples of such alcohols are NEODOL alcohol, trademark of and sold by Shell Oil Col, such as NEODOL 23 alcohol, NEODOL 25 alcohol, NEODOL 1418 alcohol; TERGITOL-L, trademark of Union Carbide Corp., such as TERGITOL-L 125 alcohol; LIAL alcohols, trademark of and sold by Liquichimica Co. such as LIAL 125; and isodecyl and tridecyl alcohols, sold by Exxon Corp., such as isodecyl alcohol and tridecyl alcohol, Guebet alcohols can also be ethoxylated. Representative examples of these alcohols are STANDAMUL alcohols, trademark of and sold by Henkel Chemical Co., such as STANDAMUL GT-12 alcohol, STANDAMUL GT-16 alcohol, STANDAMUL GT-20 alcohol, STANDAMUL GT-1620 alcohol. Secondary alcohols can also be used, such as TERGITOL 15 alcohol, trademark of and sold by Union Carbide Corp.

Generally, useable alcohols include 1-decanol; 1-undecanol; 1-dodecanol; 1-tricecanol; 1-tetradecanol; 1-pentadecanol; 1-hexadecanol; 1-heptadecanol; 1-octadecanol; 1-nonadecanol; 1-eicosanol; 1-dicosanol; 2-methyl-1-undecanol 2propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 3-octadecanol; 4-octadecanol; 5-octadecanol; 6-octadecanol; 7-octadecanol; 8-octadecanol; 9-octadecanol; 9-octadeanol-1; 2,4,6-trimethyl-1-heptanol; 2,4,6,8-tetramethyl-1-nonanol; 3,5,5-trimethyl-1-hexanol; 3,5,5,7,7-penta methyl-1-octanol; 3-butyl-1-nonanol; 3-butyl-1-; undecanol; 3-hexyl-1-undecanol; 3-hexyl-1-tridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-non-anol; 2-methyl-3-undecanol; 2-methyl-4-undecanol; 4-methyl-2-undecanol; 5-methyl-2-undecanol; 4-ethyl-2-decanol; 4-ethyl-3-decanol.

Also employable as the reactive hydrogen compound are the difunctional propylene oxide polymers having a molecular weight of 1000 to 5000, and preferably 1700 to 4100. The propylene oxide polymers having a molecular weight of 1000 to 5000 contain from 17 to 86 oxypropylene units in the molecular. These compounds are well known, being generally obtained by polymerization of propylene oxide or by the addition of propylene oxide to lower molecular compounds with 2 to 6 carbon atoms containing at least 2 reactive hydrogen atoms.

Alkylene oxides which may be employed in accordance with the invention include those alkylene oxides having between about 2 and about 4 carbon atoms and include, for example, ethylene oxide, 1,2-propylene oxide, and butylene oxides such as 1,2-butylene oxide, and mixtures thereof. The number of moles of alkylene oxides employed according to the present invention may vary widely depending on the reactive hydrogen compound to be adducted and the particular application for which the surface active agent is to be employed. In general between about 2 and about 80 or greater moles of alkylene oxide per mole of reactive hydrogen compound may be employed with greater molar ratios being employed if higher molecular weight products are desired. Insofar as propylene oxide and/or butylene oxide are used in combination with ethylene oxide, the molar ratio of ethylene oxide to propylene oxide and/or butylene oxide may be between about 50:1 and about 1:50, preferably between 3:1 to 1:3.

In the process of the invention, the reaction of an alkylene oxide with a reactive hydrogen compound is carried out in the presence of an oxyalkylation catalyst comprising a catalytic effective amount of a barium alkoxide, barium phenoxide, barium hydroxide, hydrates thereof, or mixtures thereof which are preferably soluble in the reactants and the reaction products produced thereby. However, for practical reasons the amount of the barium compound, as above noted, is preferably between about 0.1 and about 1.0 weight percent is employed, based upon the weight of the alcohol to be reacted. Suitable barium alkoxides more especially those alkoxides having alcohol moieties which are the same or similar to the reactive hydrogen compound component of the oxyalkylation reaction or those which have an alciohol moiety having at least about 8 carbon atoms, and phenoxides.

While barium alkoxides for use in accordance with the invention may be prepared by those methods known in the art, a particularly preferred barium alkoxide for use as a catalyst in the invention may be prepared by the method disclosed in copending application U.S. Ser. No. 079,497 wherein barium alkoxides of higher alcohols having more than 4 carbon atoms, and particularly, having an alcohol moiety that is the same or similar to the alcohol reactive hydrogen component are disclosed.

Barium alkoxides are, in general, prepared by a two step process. In the first step of the process, for example, a barium-containing raw material such as barium metal, or the hydrides or acetylide is reacted with a lower aliphatic alcohol having between about 4 and about 25 carbon atoms. The concentration of metal in the lower alcohol may vary from 0.01 to 20 percent. In the second step, the lower alcohol metal alkoxide reaction product is mixed with a higher alcohol having at least 4, and preferably at least 8, carbon atoms to form the metal alkoxide thereof which is employed to provide the catalyst for the oxyalkylation reaction. The barium alkoxide prepared thereby preferably has an alcohol moiety which is the same or similar to the reactive hydrogen component used in the oxyalkylation reaction mixture and is soluble in said reactive hydrogen component. The lower alcohol (alcohol having between about 4 and about 25 carbon atoms) introduced with the lower barium alkoxide is removed from the final barium alkoxide reaction product by any separation means that retains the catalytic activity of the barium alkoxide with distillation being the generally preferred means of separation.

Phenoxides of barium which are suitable for use in accordance with the invention may be prepared by reacting phenols with the certain basic salts of barium such as its alkoxides. Preferably the phenoxide is prepared by adding the phenol to the lower alcohol-barium alkoxide, prepared as above-described. The amount of the phenol added is not narrowly critical. It can vary from a few hundredths of a molar equivalent based on alkoxide to several equivalents. Illustrative of phenols suitable for use are phenol, orthocresol, metacresol, paracresol, 2,4-dialkylphenols, 2,5-dialkylphenols, nonylphenol, octylphenol, hydroquinone, and pyrogallol.

The terms "oxyalkylation promoter" or "promoter" as used herein are used herein to refer to the group of oxyalkylation catalyst promoters selected from the group consisting of superphosphoric acid, phosphoric acid, alkali metal and alkaline earth metal dihydrogen phosphates, alkali metal and alkaline earth metal dihydrogen diphosphates, alkyl, aryl, araalkyl and alkylaryl dihydrogen phosphates, oxides of phosphorus, including phosphorous pentoxide and diphosphorus trioxide, carbon dioxide and oxalic acid. When the acid compound is an alkyl dihydrogen phosphate and/or dihydrogen diphosphate the alkyl moiety preferably contains between 1 and about 25 carbon atoms, preferably between 1 and about 10 carbon atoms, and may be branched or linear.

The oxyalkylation catalyst used in accordance with the invention consists of a barium alkoxide, barium phenoxide, barium hydroxide, hydrates thereof or mixtures thereof and an oxyalkylation promoter. The amount of the oxyalkylation promoter employed is not narrowly critical with a catalytic effect having been observed employing only small amounts of the barium salts and of the promoter. The concentration of the barium compound may be between about 0.001 percent and about 20 percent by weight of the weight of the reactive hydrogen compound and is preferably between about 0.01 and about 10 percent by weight. In general, the concentration of the promoter can vary between about 0.001 percent by weight and about 30 percent by weight of the barium salt employed. Concentrations of the barium salt within the range between about 0.05 percent and about 5.0 percent by weight are usually preferred. The reaction rate, however, is generally dependent on both the process temperature, the concentration of barium salt and the concentration of promoter employed. In general, to achieve a given rate, more oxyalkylation catalyst is required at a low process temperature than that which is required at a higher process temperature. The solubility of the barium salt(s) and the promotor in the reaction mixture is also an important factor in achieving a suitable reaction rate and preventing a long induction period, and preferably, are substantially soluble in the reaction mixture. Barium compound(s) and promoter(s) that are only partially soluble in the reaction mixture at ambient conditions or at the process temperature however, may be suitable if the soluble portion provides a catalytically effective concentration of the barium compound(s) and the promoter(s).

The products prepared by the reaction of the reactive hydrogen compound and the alkylene oxide are, in general, a mixture of relatively low molecular weight alkoxylates (molecular weight up to about 5000) which are efficient nonionic surfactants wherein the molecular weight distribution of the alkoxylate species in the mixture is narrower than that obtained using conventional alkali metal catalysts, such as potassium hydroxide, or by use of only the barium compound(s); i.e., without an oxyalkylation catalyst promoter. Thus, the alkoxylate products are prepared having a greater proportion of the desired alkoxylate species, that is, having a greater proportion of products with the desired number of alkylene oxide groups per mole of active hydrogen compounds, e.g., alcohol. Moreover, products prepared in accordance with the invention generally have a smaller amount of unreacted alcohol and have a smaller amount of the undesirable poly(alkylene glycol) by-products formed. In addition, the products generally exhibit improved properties, such as a lower pour points, as compared to products prepared by the reaction of comparable amounts of alkylene oxide and alcohol reactants in the presence of conventional alkaline catalysts or solely with a barium salt.

The invention will become more clear when considered together with the following examples which are set forth as being merely illustrative of the invention and which are not intended, in any manner, to be limitative thereof. Unless otherwise indicated, all parts and percentages are by weight.

EXPERIMENTAL PROCEDURE

All examples, except as may be noted, were carried out in a 2.0 gallon stirred stainless steel autoclave equipped with automatic temperature and pressure controllers. The selected reactive hydrogen compound, barium compound, and promoter were placed in the autoclave at room temperature and purged three times with nitrogen. The reactor was heated to the reaction temperature of 140° C. and then pressurized to 20 psig with nitrogen. Alkylene oxide was added from a calibrated tank until the pressure reached about 60 psig (pounds per square inch, gauge). Thereafter, as alkylene oxide reacted and the pressure fell, more alkylene oxide was automatically added to maintain the pressure at about 60 psig. When the desired amount of oxide had been added, the feed tank was valved off and the pressure was allowed to fall. When constant pressure was reached, the reactor was cooled and discharged. Generally, the final products were neutralized to pH 7 with acetic acid or phosphoric acid and filtered. The product was derivatized with a silane (trimethylsilyl derivative) before analysis by gas chromatography. The gas chromatographic analysis was carried out on a Hewlett Packard Model No. 5830A equipped with a flame ionization detector. The column consisted of a 4 foot×⅛ inch (O.D.) stainless steel column packed with Chromosorb W (Trademark of Johns-Manville Filtration and Materials Div.) which has been acid washed and DMCS (treated) prior to Application of 2% OV-1 (Trademark of Ohio Valley Specialty Chemical Co.). The analysis was carried out using a 1.1 microliter sample size with helium as the carrier gas (flow rate of 25 cubic centimeters/minute) with the column temperature being increased during the analysis from about 70° C. to about 340° C. at the rate of about 3° C. per minute.

EXAMPLE 1

A barium alkoxide was prepared by reacting barium metal (11.95 grams) with ethanol (100 milliliter) after which 2-ethylhexanol (600 grams) was added and substantially all the ethanol was removed in vacuo.

Phosphoric acid (2.34 grams) was added to the above mixture while the mixture was stirred. The resulting mixture (599 grams thereof) was placed in an autoclave and reacted with ethylene oxide, according to the above Experimental Procedure, under pressure with the pressure being maintained at about 60 psig by the addition of ethylene oxide when the pressure fell below 60 psig. When the amount of reacted ethylene oxide corresponded to the desired average mole ratio of ethylene oxide per mole of alcohol (about 1525 milliliter) the autoclave was cooled and the product neutralized with acid to a pH of about 7. In the instant example the reaction took place over a period of about 31 minutes with about 1525 milliliters (ml) of ethylene oxide (density at 20° C. of 0.865 grams per cubic centimeter) being consumed in the reaction. The product, a poly(ethylene oxide) adduct of 2-ethylhexanol, had a molecular weight of about 446 and a 1 percent aqueous solution had a cloud point of 69° C. The analysis (based on the moles of ethylene oxide per mole of alcohol) of the trimethylsilyl derivative is shown in Table I.

TABLE I

| | Example[b] | | | | | | | | | | | |
|---|---|---|---|---|---|---|---|---|---|---|---|---|
| | 1 | 2 | 3 | 4 | 6 | 7 | 8 | 9 | 10 | 11 | 12 | 13 |
| Unreacted Alcohol | 15.7 | 8.9 | 6.3 | 2.6 | 6.0 | 2.6 | 3.1 | 4.6 | 3.9 | 2.3 | 2.0 | 3.0 |
| Alcohol[a] | | | | | | | | | | | | |
| $E_1$ | 2.3 | 1.5 | 1.8 | 2.0 | 1.7 | 2.3 | 3.7 | 3.7 | 1.5 | 1.9 | 1.0 | 1.6 |
| $E_2$ | 2.0 | 2.2 | 2.4 | 3.2 | 2.2 | 3.7 | 5.7 | 5.7 | 2.2 | 3.2 | 1.6 | 2.9 |
| $E_3$ | 3.8 | 4.0 | 4.2 | 5.4 | 3.7 | 6.5 | 8.0 | 8.0 | 4.0 | 5.6 | 2.9 | 5.3 |
| $E_4$ | 5.5 | 7.1 | 7.4 | 8.3 | 6.6 | 9.8 | 9.9 | 9.7 | 7.1 | 8.6 | 4.9 | 8.4 |
| $E_5$ | 7.5 | 11.4 | 11.9 | 11.5 | 11.1 | 13.0 | 11.1 | 10.6 | 11.2 | 11.8 | 8.9 | 11.9 |
| $E_6$ | 9.2 | 15.3 | 15.7 | 13.1 | 15.4 | 14.7 | 11.4 | 10.8 | 15.4 | 14.2 | 12.9 | 14.6 |
| $E_7$ | 11.0 | 16.3 | 16.3 | 14.8 | 17.2 | 14.3 | 11.3 | 10.6 | 16.9 | 14.6 | 15.8 | 14.9 |
| $E_8$ | 11.0 | 14.3 | 13.6 | 12.8 | 15.0 | 12.2 | 10.5 | 9.9 | 14.8 | 12.7 | 16.0 | 13.0 |
| $E_9$ | 9.7 | 9.9 | 9.4 | 10.4 | 10.4 | 9.1 | 9.0 | 8.6 | 10.8 | 9.9 | 13.5 | 10.1 |
| $E_{10}$ | 8.0 | 5.4 | 5.4 | 7.2 | 6.1 | 6.0 | 7.1 | 7.0 | 6.5 | 6.9 | 9.7 | 7.1 |
| $E_{11}$ | 6.0 | 1.7 | 2.6 | 4.4 | 3.0 | 3.4 | 5.0 | 5.2 | 3.6 | 4.3 | 6.1 | 4.4 |
| $E_{12}$ | 4.2 | 1.0 | 1.5 | 2.3 | 1.2 | 1.7 | 3.0 | 3.4 | 1.6 | 2.4 | 3.2 | 2.1 |
| $E_{13}$ | 2.5 | 0.1 | 1.1 | 1.0 | 0.4 | 0.6 | 1.2 | 1.7 | 0.5 | 1.2 | 1.3 | 0.6 |
| $E_{14}$ | 1.3 | — | 0.4 | 0.3 | — | 0.1 | — | 0.5 | — | 0.3 | 0.4 | — |
| $E_{15}$ | 0.4 | — | — | — | — | — | — | — | — | — | — | — |
| $E_{16}$ | 0.1 | — | — | — | — | — | — | — | — | — | — | — |

[a]$E_1$ is the one-mole ethylene oxide adduct, $E_2$ is the two-mole ethylene oxide adduct, etc.
[b]given as an area percent of the total area.

EXAMPLE 2

This example shows the use of phosphoric acid as the oxyalkylation promoter with a barium alkoxide. A total mixture containing 610 grams of 1-dodecanol and 0.0446 moles of barium alkoxide per 1000 of grams of the mixture, was prepared by reacting barium metal with ethanol with subsequent addition to 1-dodecanol with removal therefrom of the ethanol in vacuo. To this mixture was added, with stirring, phosphoric acid (0.89 grams). This mixture (about 600 grams thereof) was employed according to the procedure of Example 1 with a total of about 1065 milliliter (ml) of ethylene oxide reacting over a period of about 78 minutes. The product, a poly(ethylene oxide) adduct of 1-dodecanol, had a molecular weight of about 482 and a cloud point (1 percent aqueous) of 48.5° C. Gas chromatographic analysis of the trimethylsilyl derivative of the product gave the molecular weight distribution shown in Table I.

EXAMPLE 3

This example illustrates the use of a higher concentration of phosphoric acid than employed in Example 2. To 666 grams of the barium alkoxide mixture of Example 2, containing 0.0441 moles of barium alkoxide per 1000 grams of mixture, was added 1.41 grams of phosphoric acid, with stirring. The autoclave conditions of Example 1 were employed with the mixture (564 grams thereof) reacting with 1000 milliliter of ethylene oxide over a period of about 117 minutes. The product had a molecular weight of 437 and a cloud point (1 percent aqueous) of 47.5° C. Gas chromatographic analysis of the trimethylsilyl derivative of the product gave the molecular distribution shown in Table I.

EXAMPLE 4

This is a comparative example employing a barium alkoxide as the oxyalkylation catalyst without the use of phosphoric acid as an oxyalkylation promoter. A 600 gram sample of a mixture containing 0.045 moles of alkoxide per 1000 grams of the mixture was prepared as in Example 3 and was reacted with ethylene oxide in an autoclave and at the conditions as set forth in Example 1. Over an 80 minute period 1065 milliliters of ethylene oxide reacted with the mixture. The final product had a molecular weight of 492 and a cloud point (1 percent aqueous) of 57.5° C. Gas chromatographic analysis of the trimethylsilyl derivative of the product is set forth in Table I.

EXAMPLE 5

This example is a comparative example showing that phosphoric acid by itself is not effective as an oxyalkylation catalyst. Phosphoric acid (1.41 grams) was added to a one-liter flask containing 600 grams of 1-dodecanol with thorough mixing, and the oxyalkylation reaction was carried out according to the procedure of Example 1 with the mixture reacting with less than 60 milliliters of ethylene oxide over a period of about 125 minutes.

EXAMPLE 6

This example shows the use of phosphoric acid as an oxyalkylation promoter, according to the instant invention, with barium hydroxide monohydrate to provide the oxyalkylation catalyst. To 600 grams of 1-dodecanol was added 16.48 grams of barium hydroxide monohydrate. This mixture was heated to 110° C. in vacuo and cooled. Phosphoric acid (2.76 grams) was then added to the mixture and the mixture was again heated to 110° C. in vacuo. A 581 gram sample of this mixture was placed in an autoclave, as in Example 1, and reacted with 1035 milliliters of ethylene oxide over a period of 188 minutes. The product had a molecular weight of 494 and a cloud point (1 percent aqueous) of 52.5° C. Gas chromatographic analysis of the trimethylsilyl derivative of the product is given in Table I.

EXAMPLE 7

This comparative example shows the use of a catalyst prepared in accordance with U.S. Pat. No. 4,239,917, wherein a oxyalkylation catalyst promoter is not employed therewith. A mixture of barium hydroxide (15.15 grams) was mixed with 1-dodecanol (550 grams) and the resulting mixture heated at 110° C. at 5 millimeters mercury pressure. The mixture (548 grams thereof) was employed as an oxyalkylation catalyst according to the procedure of Example 1 with 950 milliliters of ethylene oxide reacting over a period of 135 minutes. The product had a molecular weight of 480 and a cloud point (1 percent aqueous) of 50° C. Gas chromoatographic analysis of the acetate derivative gave the molecular distribution set forth in Table I.

EXAMPLE 8

This comparative example shows the broad molecular distribution obtained when a strong base catalyst is employed as the oxyalkylation catalyst. To 1-dodecanol (525 grams) there was added potassium hydroxide (12.69 grams; 33 percent aqueous solution). The mixture was heated to 110° C. at a pressure of 5 millimeters mercury. A sample of the resulting mixture (500 grams thereof) was employed in the oxyalkylation reaction, as in Example 1, and reacted with 1080 milliliters of ethylene oxide over a period of 63 minutes. The product had a molecular weight of 495 grams and a cloud point (1 percent aqueous) of 55° C. The gas chromatographic analysis of the acetate derivative of the product is shown in Table I.

EXAMPLE 9

This comparative example shows that phosphoric acid has a deleterious effect on the formation rate of product when employed with a strong base catalyst(s). Potassium hydroxide (11.09 grams as a powder) was added to 1200 grams of 1-dodecanol. The resulting mixture was heated to 100° C. at a pressure of 5 milliliter mercury. Phosphoric acid (1.90 grams) was then added to the mixture and the mixture was heated at 100° C. in vacuo. A 590 gram sample of this mixture was reacted with ethylene oxide, according to Example 1, over a period of 113 minutes with 1050 milliliters of ethylene oxide reacting. The product had a molecular weight of 488 grams and a cloud point (1 percent aqueous) of 53° C. Gas chromatographic analysis of the acetate derivative of the product gave the molecular distribution shown in Table I.

EXAMPLE 10

This example shows the promotional effect of phosphoric acid on the barium catalyst of U.S. Pat. No. 4,210,764, incorporated herein by reference thereto. Barium hydroxide monohydrate (16.48 grams) and phenol (16.38 grams) were added to 603 grams of 1-dodecanol. This mixture was heated to 110° C. at a pressure of 5 millimeter mercury. Phosphoric acid (2.76 grams) was added to this mixture and the mixture again heated to 110° C. at a 5 millimeter pressure. A 609 gram sample of this mixture was reacted with ethylene oxide, as in Example 1, with 32 minutes being required to react 1080 milliliters of ethylene oxide. The product had a molecular weight of 485 and a cloud point (1 percent aqueous) of 55.5° C. Gas chromatographic analysis of the trimethylsilyl derivative of the product gave the molecular distribution shown in Table I.

EXAMPLE 11

This example is a comparative which shows the use of the barium catalyst according to U.S. Pat. No. 4,210,764 without an oxyalkylation promoter formed by mixing barium hydroxide monohydrate (16.48 grams) phenol (16.38 grams) to 600 grams of 1-dodecanol. This mixture was then heated to 110° C. at a pressure of 5 millimeters mercury. A 618 gram sample of this mixture was employed, according to the procedure of Example 1, with 43 minutes being required to react 1100 milliliters of ethylene oxide. The molecular weight of the product was 485 and the cloud point (1 percent aqueous) was 54° C. Gas chromatograph analysis of the trimethylsilyl derivative of the product is shown in Table I.

EXAMPLE 12

This example shows the use of a barium alkoxide and phosphoric acid in the oxalkylation of LIAL-125 (a mixture of $C_{12}$–$C_{15}$ primary alcohols, 40% normal, 60% branched). A mixture of barium metal (11.95) grams) and ethanol (1000 milliliters) was added to 600 grams of LIAL-125. The ethanol was removed by heating the mixture to 90° C. at a pressure of 5 millimeters mercury with the resulting mixture containing 0.051 moles of barium ethoxide per 1000 grams of the mixture. Phosphoric acid (0.038 moles) was added to this mixture with stirring. This mixture (601 grams thereof) was used in the oxyalkylation reaction, according to Example 1, with 20 minutes being required to react 950 milliliters of ethylene oxide. The product (a poly(ethylene oxide) adduct of LIAL-125) had a molecular weight of 513.

We claim:

1. The method for the alkoxylation of a reactive hydrogen compound, selected from the group consisting of monohydric alcohols having between about 8 to about 25 carbon atoms and a difunctional poly(propylene oxide) polymer having an average molecular weight in the range of 1,000 to 5,000, comprising contacting said hydrogen compound with an alkylene oxide having between 2 and 4 carbon atoms in the presence of a catalyst selected from the group consisting of barium alkoxides, barium phenoxides, barium hydroxides, hydrates thereof or mixtures thereof and an oxyalkylation catalyst promoter selected from the group consisting of superphosphoric acid, phosphoric acid, alkali metal and alkaline earth metal dihydrogen phosphates and dihydrogen diphosphates, alkyl, aryl, araalkyl and alkyaryl dihydrogen phosphates, phosphorous trioxide, and carbon dioxide at a temperature between about 50° C. and about 400° C. employing about 2 to about 80 moles of alkylene oxide per mole of reactive hydrogen compound.

2. The method of claim 1 wherein the catalyst is a barium alkoxide.

3. The method of claim 1 wherein the reactive hydrogen compound is a product of a hydroformylation/hydrogenation reaction.

4. The method of claim 1 wherein the reaction is carried out at a pressure between about 10 psig and 100 psig.

5. The method of claim 1 wherein the catalyst is present in an amount between about 0.1 and about 1.0 percent by weight based upon the weight of alcohol.

6. The method of claim 1 wherein the reactive hydrogen compound is an alkanol which is a linear alcohol containing between about 7 and about 20 carbon atoms, the alkylene oxide is ethylene oxide, the catalyst is a barium alkoxide and the oxyalkylation promoter is phosphoric acid.

7. The method of claim 1 wherein the oxyalkylation catalyst promoter is selected from the group comprising superphosphorus acid, phosphoric acid, oxides of phosphorus and phosphorus acid.

* * * * *